United States Patent [19]

Theobald et al.

[11] Patent Number: 5,344,813
[45] Date of Patent: Sep. 6, 1994

[54] HYDROXYPYRIDONECARBOXAMIDES, THEIR MANUFACTURE AND USE AS HERBICIDES

[75] Inventors: Hans Theobald, Limburgerhof; Wolfgang von Deyn, Neustadt; Christoph Nuebling, Hassloch; Helmut Walter, Obrigheim; Uwe Kardorff, Mannheim; Karl-Otto Westphalen, Speyer, all of Fed. Rep. of Germany; Thomas Kappe, Graz, Austria; Matthias Gerber, Mutterstadt, Fed. Rep. of Germany

[73] Assignee: BASF Aktiengesellschaft, Ludwigshafen, Fed. Rep. of Germany

[21] Appl. No.: 981,361

[22] Filed: Nov. 25, 1992

[30] Foreign Application Priority Data

Nov. 26, 1991 [DE]  Fed. Rep. of Germany ....... 4138819

[51] Int. Cl.$^5$ ................. A01N 43/40; C07D 213/56
[52] U.S. Cl. ................................ 504/244; 546/296
[58] Field of Search ..................... 546/296; 504/244

[56] References Cited

U.S. PATENT DOCUMENTS 4,631,081  12/1986  Watson et al. ............... 504/244

FOREIGN PATENT DOCUMENTS 0104876  4/1984  European Pat. Off. ............ 504/244

*Primary Examiner*—Alan L. Rotman
*Attorney, Agent, or Firm*—Keil & Weinkauf

[57] ABSTRACT

Hydroxypyridonecarboxamides of the formula I

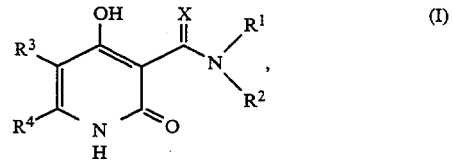

where:
X is oxygen or sulfur;
$R^1$, $R^2$ independently of each other are hydrogen, alkyl, alkenyl, alkynyl, cycloalkyl, cycloalkylalkyl or alkoxy, and these organic radicals are substituted or unsubstituted;
$R^3$ is hydrogen, alkyl, haloalkyl, alkoxy, haloalkoxy, alkylthio, haloalkylthio, halogen or nitro;
$R^4$ is alkyl, alkenyl, alkynyl, cycloalkyl, alkoxy, alkylthio, phenyl or a 5- or 6-membered heterocyclic, aliphatic or aromatic radical containing from one to three heteroatoms selected from the group consisting of oxygen, sulfur and nitrogen, and these radicals are substituted or unsubstituted;
with the exception of 6-methyl-4-hydroxypyrid-2-one-3-carboxamide and 6-methyl-4-hydroxypyrid-2-one-3-carboxylic acid-tert-butylamide.

8 Claims, No Drawings

HYDROXYPYRIDONECARBOXAMIDES, THEIR MANUFACTURE AND USE AS HERBICIDES

The present invention relates to hydroxypyridonecarboxamides of the formula I

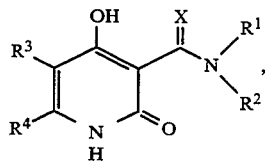

where:

X is oxygen or sulfur;

$R^1$, $R^2$ independently of each other are hydrogen, straight-chain or branched $C_1$-$C_{25}$-alkyl, $C_3$-$C_{25}$-alkenyl, $C_3$-$C_{25}$-alkynyl, $C_3$-$C_8$-cycloalkyl, $C_3$-$C_8$-cycloalkyl-$C_1$-$C_{17}$-alkyl or $C_1$-$C_{25}$-alkoxy, the organic radicals being unsubstituted or substituted by halogen, cyano, $C_1$-$C_5$-alkylcarbonyl, $C_1$-$C_5$-alkoxycarbonyl, $C_1$-$C_6$-alkoxy, $C_1$-$C_6$-haloalkoxy, $C_1$-$C_6$-alkylthio, $C_1$-$C_6$-haloalkylthio, substituted or unsubstituted phenyl, substituted or unsubstituted heterocyclyl or by a substituted or unsubstituted heteroaromatic radical;

$R^3$ is hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen or nitro;

$R^4$ is $C_1$-$C_{10}$-alkyl, $C_2$-$C_{10}$-alkenyl, $C_2$-$C_{10}$-alkynyl, $C_3$-$C_{10}$-cycloalkyl, $C_1$-$C_{10}$-alkoxy, $C_1$-$C_{10}$-alkylthio, phenyl or a 5- or 6-membered heterocyclic, aliphatic or aromatic radical containing from one to three heteroatoms selected from the group consisting of oxygen, sulfur and nitrogen, the said radicals being unsubstituted or substituted by halogen, $C_1$-$C_3$-alkyl, $C_1$-$C_3$-haloalkyl, $C_1$-$C_3$-alkoxy, $C_1$-$C_3$-haloalkoxy, $C_1$-$C_3$-haloalkylthio, substituted or unsubstituted phenyl or a substituted or unsubstituted heterocyclic radical as mentioned above;

and salts thereof, with the exception of 6-methyl-4-hydroxypyrid-2-one-3-carboxamide and 6-methyl-4-hydroxypyrid-2-one-3-carboxylic acid-tert-butylamide.

The present invention further relates to the manufacture of compounds I and their use as herbicides.

2-Hydroxypyridonecarboxamides have already been disclosed in the literature, namely 6-methyl-4-hydroxypyrid-2-one-3-carboxamide (EP-A-104876) and 6-methyl-4-hydroxypyrid-2-one-3-carboxylic acid-tert-butylamide (Dissertation by Ahmed Fahrny Ali Khattab, University of Graz, 1990). However, herbicidal actions of these compounds have not been disclosed.

The object of the invention was to provide hydroxypyridonecarboxamides having a good herbicidal action. This object was achieved with the compounds described at the outset, methods for preparing them, and herbicidal agents containing these compounds.

The hydroxypyridonecarboxamides I may be present in the following tautomeric forms:

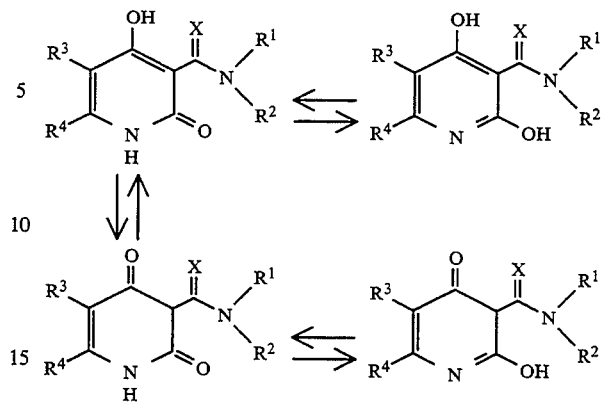

The hydroxypyridonecarboxamides I are prepared by reacting compounds of the formula II

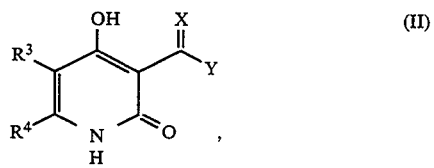

where X, $R^3$ and $R^4$ have the above meanings and Y is a halogen atom, an OH group or an alkoxy group, with an amine of the formula III

where $R^1$ and $R^2$ have the above meanings, under suitable, generally known conditions.

Particularly advantageously, alkyl esters (Y=O-alkyl), e.g., methyl or ethyl esters, are reacted with the amines of the formula III. This amidation takes place generally at from 50°–250° C., preferably 110°–160° C., with stirring, or in an autoclave.

Suitable solvents are alcohols such as methanol, ethanol and propanol, and hydrocarbons such as benzene or toluene, water, ether such as diethyl ether or tetrahydrofuran, and aprotic dipolar solvents such as dimethylformamide, dimethyl sulfoxide or pyridine.

Mixtures of these compounds may also be used as solvents and diluents.

The starting materials are usually reacted with each other in stoichiometric amounts. To increase the yield, for instance, it may be advantageous to use one of the starting materials, preferably the amine, in an excess of from 0. 1 to 10 mole equivalents.

The amidation is generally carried out at atmospheric pressure. However, it may, depending on the type of amine or solvent used, be advantageous to run the reaction at super-atmospheric pressure, especially autogenously increased pressure, in an autoclave.

The manufacture of the starting compounds is disclosed in: J. Met. Chem. 20 (5), 1363 (1983); Synthesis (6), 479 (1988); Liebigs Ann. Chem. (3), 371 (1979); Synth. Commun. 7 (2) 149 (1977).

The amines of the formula III required for the reaction are well-known or commercially available, or may be prepared by generally known chemical processes.

In view of the use for which the hydroxypyridonecarboxamides of the formula I are intended, the following radicals are suitable substituents:

$R^1$, $R^2$ hydrogen;

unbranched or straight-chain $C_1$–$C_{25}$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl, 1-ethyl-2-methylpropyl, heptyl, 1-methylheptyl, octyl, nonyl, decyl, undecyl, dodecyl, tridecyl, tetradecyl, pentadecyl, hexadecyl, heptadecyl, octadecyl, nonadecyl, arachidyl, heneicosanyl, docosyl, tricosyl, tetracosyl and pentacosyl; especially $C_1$–$C_{15}$-alkyl, for example $C_1$–$C_6$-alkyl, such as methyl, ethyl, 1-methylethyl, 1-methylpropyl, 2-methylpropyl, 1,1-dimethylethyl and 1,1-dimethylpropyl;

unbranched or straight-chain $C_3$–$C_{25}$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and ethyl-2-methyl-2-propenyl, 10-undecenyl, 9-tetradecenyl, 9-hexadecenyl, 6-octadecenyl, 9-octadecenyl, 11-octadecenyl, 9,12-octadecadienyl, 11-eicosenyl, 13-eicosenyl and 13-docosenyl;

especially $C_3$–$C_{15}$-alkenyl, for example $C_3$–$C_6$-alkenyl, such as 2-propenyl, 2-butenyl, 3-butenyl, 1-methyl-2-propenyl, 2-methyl-2-propenyl and 1-methyl-2-butenyl;

$C_3$–$C_{25}$-alkynyl, especially $C_3$–$C_{15}$-alkynyl; and particularly preferably $C_3$–$C_6$-alkynyl, e.g., propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

$C_3$–$C_8$-cycloalkyl, such as cyclopropyl, cyclobutyl, cyclopentyl, cyclohexyl, cyclohe[ptyl and cyclooctyl, especially cyclopropyl and cyclohexyl;

$C_1$–$C_{25}$-alkoxy, especially $C_1$–$C_{15}$-alkoxy, the alkyl radical having the meanings given above, particularly preferably $C_1$–$C_4$-alkoxy, such as methoxy, ethoxy, n-propoxy, isopropoxy, n-butyloxy, isobutyloxy and tert-butyloxy;

it being possible for these groups to bear from one to five halogen atoms such as fluorine, chlorine, bromine and iodine, especially fluorine and chlorine, and/or from one to three of the following radicals:

cyano;

$C_1$–$C_5$-alkyl- or -alkoxycarbonyl, where the alkyl and alkoxy structural elements have the meanings given individually above, e.g., methylcarbonyl and methoxycarbonyl;

$C_3$–$C_8$-cycloalkyl, such as cyclopropyl, cyclobutyl, cyclopentyl, cyclohexyl, cycloheptyl and cyclooctyl, especially cyclopropyl and cyclohexyl;

$C_1$–$C_6$-alkoxy, such as methoxy, ethoxy, n-propoxy, 2-methylethoxy, n-butoxy, 1-methylpropoxy, 2-methylpropoxy and 1,1-dimethylethoxy, n-pentoxy, n-hexoxy, especially $C_1$–$C_3$-alkoxy, such as methoxy, ethoxy, isopropoxy;

$C_1$–$C_6$-haloalkoxy, such as chloromethoxy, dichloromethoxy, trichloromethoxy, fluoromethoxy, difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, especially $C_1$–$C_3$-haloalkoxy, such as 2,2,2-trifluoroethyloxy and 2-chloro-2,2-difluoroethoxy;

$C_1$–$C_6$-alkylthio, such as methylthio, ethylthio, n-propylthio, 1-methylethylthio, n-butylthio, 1-methylpropylthio, 2-methylpropylthio and 1,1-dimethylethylthio, especially $C_1$–$C_3$-alkylthio, such as methylthio and ethylthio;

$C_1$–$C_6$-haloalkylthio, such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio and pentafluoroethylthio, especially $C_1$–$C_3$-haloalkylthio, such as trichloromethylthio;

phenyl, where the phenyl radicals in turn may bear from one to five halogen atoms such as fluorine, chlorine, bromine and iodine, especially fluorine and chlorine, and/or from one to three of the following groups:

cyano or nitro;

$C_1$–$C_4$-alkyl, as mentioned above, especially methyl, ethyl, propyl, 1-methylpropyl and 1,1-dimethylpropyl;

$C_1$–$C_4$-alkoxy, as mentioned above, especially methoxy and ethoxy;

$C_1$–$C_4$-haloalkyl, as mentioned above, especially trifluoromethyl;

$C_1$–$C_4$-haloalkoxy, as mentioned above, especially trifluoromethoxy;

a 5- to 6-membered heterocyclic, aliphatic or aromatic radical containing one to three heteroatoms selected from the group consisting of oxygen, sulfur and nitrogen, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrrolyl, 3-pyrazolyl, 4-pyrazolyl , 5-pyrazolyl, 2-pyridyl, 4-pyridyl, 4-pyridyl, oxa-2,4-diazolyl, oxa-3,4-diazolyl,thia-2,4-diazolyl, thia-3,4-diazolyl and triazolyl,
it being possible for these heterocyclic or heteroaromatic substituents in turn to bear one or two of the following substituents:
  halogen, such as fluorine, chlorine, bromine and iodine, especially fluorine and chlorine,
  $C_1$–$C_3$-alkyl or $C_1$–$C_3$-alkoxy, as mentioned above;
$R^3$
  hydrogen;
  halogen, such as fluorine, chlorine, bromine and iodine, especially fluorine and chlorine;
  nitro;
  $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio and $C_1$–$C_6$-haloalkylthio, each as mentioned above individually for $R^1$ and $R^2$;
$R^4$
  $C_1$–$C_{10}$-alkyl, especially $C_1$–$C_6$-alkyl as mentioned above individually for $R^1$ or $R^2$. e.g., methyl, ethyl, tert.-butyl;
  $C_2$–$C_{10}$-alkenyl or $C_2$–$C_{10}$-alkynyl, especially $C_2$–$C_6$-alkenyl or $C_2$–$C_6$-alkynyl as mentioned above individually for $R^1$;
  $C_1$–$C_{10}$-alkoxy or $C_1$–$C_{10}$-alkylthio, especially $C_1$–$C_6$-alkoxy and $C_1$–$C_6$-alkylthio as mentioned above for $R^1$ or $R^2$, e.g., methoxy, ethoxy, methylthio, ethylthio;
  phenyl or a 5- to 6-membered, heterocyclic, aliphatic or aromatic radical containing from one to three heteroatoms selected from the group consisting of oxygen, sulfur and nitrogen, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl , 4-isoxazolyl, 5-isoxazolyl, 3-isothiazolyl , 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl, 4-pyridyl, oxa-2,4-diazolyl, oxa-3,4-diazolyl, thia-2,4-diazolyl, thia-3,4-diazolyl and triazolyl, and the phenyl radical and the heterocyclic and heteroaromatic radicals may bear one or two of the following substituents:
  halogen, such as fluorine, chlorine, bromine and iodine, especially fluorine and chlorine,
  $C_1$–$C_3$-alkyl, $C_1$–$C_3$-haloalkyl, $C_1$–$C_3$-haloalkoxy, $C_1$–$C_3$-alkoxy, each as mentioned above,
  phenyl or one of the heterocyclic or heteroaromatic substituents mentioned for $R^4$, and these radicals in turn may be substituted by halogen, $C_1$–$C_3$-alkyl, $C_1$–$C_3$-haloalkyl, $C_1$–$C_3$-haloalkoxy and $C_1$–$C_3$-alkoxy, each as mentioned above;
the following radicals are given by way of example: 4-chlorophenyl, 4-methylphenyl, 4-trifluoromethylphenyl, 4-methoxyphenyl, 4-trifluoromethoxyphenyl.
Examples of suitable salts of compounds I are agriculturally useful salts, for example alkali metal salts, especially the potassium and sodium salts, alkaline earth metal salts, especially the calcium, magnesium and barium salts, manganese, copper, zinc and iron salts, and ammonium, phosphonium, tetraalkylammonium salts, benzyltrialkylammonium salts, trialkylsulfonium salts or trialkylsulfoxonium salts.

Examples of particularly preferred compounds of the formula I are listed in the following table:

TABLE

Compounds of structure I

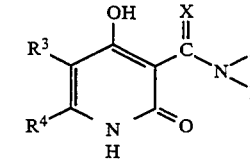

| $R^1$ | $R^2$ | $R^3$ | $R^4$ | X |
|---|---|---|---|---|
| H | methoxy | H | $CH_3$ | O |
| H | ethoxy | H | $CH_3$ | O |
| H | propoxy | H | $CH_3$ | O |
| H | benzyloxy | H | $CH_3$ | O |
| H | 2-phenoxyethyl | H | $CH_3$ | O |
| H | tert. butyl | H | $CH_3$ | O |
| H | tert. butyl | H | F | O |
| H | tert. butyl | H | $C_2H_5$ | O |
| H | isopropyl | H | $C_2H_5$ | O |
| H | isopropyl | H | $CH_3$ | O |
| H | isopropyl | H | F | O |
| H | tert. butyl | methyl | $CH_3$ | O |
| H | isopropyl | methyl | $CH_3$ | O |
| H | tert. butyl | H | $CF_3$ | O |
| H | 1,1-dimethyl-2-propenyl | H | $CH_3$ | O |
| H | 2-propynyl | H | $CH_3$ | O |
| H | 1-methyl-2-propynyl | H | $CH_3$ | O |
| H | 1,1-dimethyl-2-propynyl | H | $CH_3$ | O |
| H | benzyl | H | $CH_3$ | O |
| H | 1-methyl-phenylmethyl | H | $CH_3$ | O |
| H | 1,1-dimethylphenylmethyl | H | $CH_3$ | O |
| H | 2-phenylethyl | H | $CH_3$ | O |
| H | 2-methylthioethyl | H | $CH_3$ | O |
| H | 1-methyl-2-methylthioethyl | H | $CH_3$ | O |
| H | 2-fluoroethyl | H | $CH_3$ | O |
| H | 2-fluoro-1-methylethyl | H | $CH_3$ | O |
| H | 1,1-dimethyl-2-fluoroethyl | H | $CH_3$ | O |
| H | 2-chloroethyl | H | $CH_3$ | O |
| H | 2-chloro-1-methylethyl | H | $CH_3$ | O |
| H | 2-chloro-1,1-dimethylethyl | H | $CH_3$ | O |
| H | 2-cyanoethyl | H | $CH_3$ | O |
| H | 2-cyano-1,1-dimethylethyl | H | $CH_3$ | O |
| H | 2-chlorobenzyl | H | H | O |
| H | 4-methoxybenzyl | H | H | O |
| H | isopropyl | H | $CF_3$ | O |
| H | tert. butyl | H | phenyl | O |
| H | isopropyl | H | phenyl | O |
| H | tert. butyl | H | methoxy | O |
| H | tert. butyl | $NO_2$ | H | O |
| H | isopropyl | $NO_2$ | H | O |
| H | tert. butyl | $CH_3$ | H | O |
| H | tert. butyl | H | 1,1,2,2-tetrafluoroethoxy | O |
| H | tert. butyl | Cl | H | O |
| H | isopropyl | Cl | H | O |
| H | tert. butyl | $OCH_3$ | $OCH_3$ | O |
| H | tert. butyl | $CH_3$ | $CF_3$ | O |
| H | tert. butyl | H | — | O |
| H | tert. butyl | Br | $CH_3$ | O |
| H | tert. butyl | $NO_2$ | phenyl | O |
| $CH_3$ | methyl | H | $CH_3$ | O |
| $CH_3$ | ethyl | H | $CH_3$ | O |
| H | methoxy | H | $CH_3$ | S |
| H | ethoxy | H | $CH_3$ | S |
| H | propoxy | H | $CH_3$ | S |
| H | benzyloxy | H | $CH_3$ | S |
| H | 2-phenoxyethyl | H | $CH_3$ | S |
| H | tert. butyl | H | $CH_3$ | S |
| H | tert. butyl | H | F | S |
| H | tert. butyl | H | $C_2H_5$ | S |

TABLE-continued

Compounds of structure I

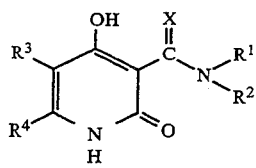

| R¹ | R² | R³ | R⁴ | X |
|---|---|---|---|---|
| H | isopropyl | H | $C_2H_5$ | S |
| H | isopropyl | H | $CH_3$ | S |
| H | isopropyl | H | F | S |
| H | tert. butyl | methyl | $CH_3$ | S |
| H | isopropyl | methyl | $CH_3$ | S |
| H | tert. butyl | H | $CF_3$ | S |
| H | 1,1-dimethyl-2-propenyl | H | $CH_3$ | S |
| H | 2-propynyl | H | $CH_3$ | S |
| H | 1-methyl-2-propynyl | H | $CH_3$ | S |
| H | 1,1-dimethyl-2-propynyl | H | $CH_3$ | S |
| H | benzyl | H | $CH_3$ | S |
| H | 1-methylphenylmethyl | H | $CH_3$ | S |
| H | 1,1-dimethylphenylmethyl | H | $CH_3$ | S |
| H | 2-phenylethyl | H | $CH_3$ | S |
| H | 2-methylthioethyl | H | $CH_3$ | S |
| H | 1-methyl-2-methylthioethyl | H | $CH_3$ | S |
| H | 2-fluoroethyl | H | $CH_3$ | S |
| H | 2-fluoro-1-methylethyl | H | $CH_3$ | S |
| H | 1,1-dimethyl-2-fluoroethyl | H | $CH_3$ | S |
| H | 2-chloroethyl | H | $CH_3$ | S |
| H | 2-chloro-1-methylethyl | H | $CH_3$ | S |
| H | 2-chloro-1,1-dimethylethyl | H | $CH_3$ | S |
| H | 2-cyanoethyl | H | $CH_3$ | S |
| H | 2-cyano-1,1-dimethylethyl | H | $CH_3$ | S |
| H | 2-chlorobenzyl | H | H | S |
| H | 4-methoxybenzyl | H | H | S |
| H | isopropyl | H | $CF_3$ | S |
| H | tert. butyl | H | phenyl | S |
| H | isopropyl | H | phenyl | S |
| H | tert. butyl | H | methoxy | S |
| H | tert. butyl | $NO_2$ | H | S |
| H | isopropyl | $NO_2$ | H | S |
| H | tert. butyl | $CH_3$ | H | S |
| H | tert. butyl | H | 1,1,2,2-tetrafluoroethoxy | S |
| H | tert. butyl | Cl | H | S |
| H | isopropyl | Cl | H | S |
| H | tert. butyl | $OCH_3$ | $OCH_3$ | S |
| H | tert. butyl | $CH_3$ | $CF_3$ | S |
| H | tert. butyl | H | — | S |
| H | tert. butyl | Br | $CH_3$ | S |
| H | tert. butyl | $NO_2$ | phenyl | S |
| $CH_3$ | methyl | H | $CH_3$ | S |
| $CH_3$ | ethyl | H | $CH_3$ | S |

The compounds I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are generally suitable for the preparation of solutions, emulsions, pastes and oil dispersions to be sprayed direct. Examples of inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.01 to 95, and preferably 0.5 to 90, % by weight of active ingredient. The active ingredients are used in a purity of 90 to 100, and preferably 95 to 100, % (according to the NMR spectrum).

Examples of formulations are as follows:
I. 90 parts by weight of compound no. 1 is mixed with 10 parts by weight of N-methyl-α-pyrrolidone. A mixture is obtained which is suitable for application in the form of very fine drops.
II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3, preferably 0.01 to 1, kg of active ingredient per hectare.

In view of the numerous application methods possible, the compounds according to the invention or the agents containing them may be used in a large number of crops. Those which follow are given by way of example:

| | |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Brassica napus* var. *napus* | rapeseed |
| *Brassica napus* var. *napobrassica* | swedes |
| *Camellia sinensis* | tea plants |
| *Carthamus tinctorius* | safflower |
| *Carya illinoinensis* | pecan trees |
| *Citrus limon* | lemons |
| *Citrus sinensis* | orange trees |
| *Coffea arabica* (*Coffea canephora*, *Coffea liberica*) | coffee plants |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum*, *Gossypium herbaceum*, *Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Musa* spp. | banana plants |
| *Nicotiana tabacum* (*N. rustica*) | tobacco |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus* spp. | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (*s. vulgare*) | sorghum |
| *Theobroma cacao* | cacao plants |
| *Trifolium pratense* | red clover |
| *Triticum aestivum* | wheat |
| *Triticum durum* | wheat |
| *Vicia faba* | tick beans |
| *Vitis vinifera* | grapes |
| *Zea mays* | Indian corn, sweet corn, maize |

To increase the spectrum of action and to achieve synergistic effects, the hydroxypyridonecarboxamides I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, sulfonylureas, (hetero)-aryloxyphenoxypropionic acids and salts, esters, amides thereof, etc.

It may also be useful to apply the novel herbicidal compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

Preparation of 4-hydroxy-6-methylpyrid-2-one-3-carboxylic acid-n-butylamide (Ex. no. 4 in Table 1)

9.85 g (0.05 mol) of ethyl 4-hydroxy-6-methylpyrid-2-one-3-carboxylate was stirred with 4.6 g (0.06 mol) of n-butylamine in 60 ml of ethanol in a miniautoclave for 8 hours at 150° C. under autogenous pressure. After cooling, the crystals were separated by suction filtration, washed with ligroin and dried.

Yield: 8.5 g (75.9% of theory); m.p.: 158° C.

Further compounds I were prepared analogously with appropriate modifications of the starting materials. The compounds thus obtained are listed in the table below with their physical data.

TABLE 1

Hydroxypyridone-3-carboxamides I

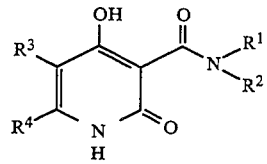

| No. | $R^1$ | $R^2$ | $R^3$ | $R^4$ | Melting point [°C.] |
|---|---|---|---|---|---|
| 1 | H | tert.-butyl | H | $CH_3$ | 241 |
| 2 | H | isopropyl | H | $CH_3$ | 203 |
| 3 | H | n-propyl | H | $CH_3$ | 202–203 |
| 4 | H | n-butyl | H | $CH_3$ | 158 |
| 5 | H | methyl | H | $CH_3$ | >260 |
| 6 | H | ethyl | H | $CH_3$ | 227 |
| 7 | H | 1-methyl-1-ethylpropyl | H | $CH_3$ | 233 |
| 8 | H | 2-methyl-n-butyl- | H | $CH_3$ | 170 |
| 9 | H | 1-methyl-n-butyl- | H | $CH_3$ | 193 |
| 10 | $CH_3$ | tert.-butyl | H | $CH_3$ | |
| 11 | $CH_3$ | $CH_3$ | H | $CH_3$ | |
| 12 | $C_2H_5$ | $C_2H_5$ | H | $CH_3$ | 95–105 |
| 13 | H | isopropyl | H | $CF_3$ | 197–203 |
| 14 | H | tert.-butyl | H | $CF_3$ | 200–203 |
| 15 | H | tert.-butyl | Br | $CH_3$ | 252–254 |
| 16 | H | isopropyl | Br | $CH_3$ | 256 |
| 17 | H | isopropyl | Cl | $CH_3$ | 221 |
| 18 | H | tert.-butyl | Cl | $CH_3$ | 257 |
| 19 | H | n-propyl | $NO_2$ | $C_2H_5$ | |
| 20 | H | isopropyl | $NO_2$ | $CH_3$ | 246 |
| 21 | H | tert.-butyl | $NO_2$ | $CH_3$ | 270 |
| 22 | H | tert.-butyl | H | phenyl | 183 |
| 23 | H | isopropyl | H | phenyl | 208 |
| 24 | H | 1,3-dimethylpropyl | H | $CH_3$ | 215 |
| 25 | H | 1-n-propyl-n-butyl | H | $CH_3$ | 203 |
| 26 | H | 1-ethyl-n-propyl | H | $CH_3$ | 205 |
| 27 | H | 1,1-dimethyl-n-propyl | H | $CH_3$ | 252 |
| 28 | H | 1,1,2-trimethylpropyl | H | $CH_3$ | 251 |
| 29 | H | 2,2-dimethylpropyl | H | $CH_3$ | 217 |
| 30 | H | 3-methyl-1(2'-methylpropyl)-butyl | H | $CH_3$ | 225–235 |
| 31 | H | 2-ethyl-n-butyl- | H | $CH_3$ | 180 |
| 32 | H | 2,4,4-trimethylpent-2-yl | H | $CH_3$ | 215 |
| 33 | H | 1-methyl-1-ethyl-n-pentyl | H | $CH_3$ | 178–179 |
| 34 | H | n-pentyl | H | $CH_3$ | 174 |
| 35 | H | 1-methyl-2-methoxyethyl | H | $CH_3$ | 187 |

TABLE 1-continued

Hydroxypyridone-3-carboxamides I

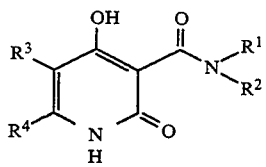

| No. | R¹ | R² | R³ | R⁴ | Melting point [°C.] |
|---|---|---|---|---|---|
| 36 | H | 1-ethyl-2-methoxyethyl | H | $CH_3$ | 186 |
| 37 | H | n-heptyl | H | $CH_3$ | 138 |
| 38 | H | n-nonyl | H | $CH_3$ | 132–142 |
| 39 | H | n-undecyl | H | $CH_3$ | 116–117 |
| 40 | H | n-pentadecyl | H | $CH_3$ | 120–121 |
| 41 | H | 1-methylpropyl | H | $CH_3$ | 143–148 |
| 42 | H | cyclopropyl | H | $CH_3$ | 247 |
| 43 | H | 2,6-difluorobenzyl | H | $CH_3$ | 260 |
| 44 | H | (+)-1-methylbenzyl | H | $CH_3$ | 203 |
| 45 | H | (−)-1-methylbenzyl | H | $CH_3$ | 203–205 |
| 46 | H | (D)-1-methylbenzyl | H | $CH_3$ | 214 |
| 47 | t-butyl | H | H | 2-F-4-methylphenyl | 178 |
| 48 | t-butyl | H | H | 4-isopropylphenyl | 143–146 |
| 49 | t-butyl | H | H | 4-fluorophenyl | 218–225 |
| 50 | isopropyl | H | $CH_3$ | $CH_3$ | 232 |
| 51 | tert.-butyl | H | $CH_3$ | $CH_3$ | 258 |
| 52 | 1-(4-methylphenyl)ethyl | H | $CH_3$ | $CH_3$ | 202–203 |
| 53 | H | isopropyl | n-butyl | $CH_3$ | 180 |
| 54 | H | t-butyl | n-butyl | $CH_3$ | 213–220 |
| 55 | H | t-butyl | ethyl | $CH_3$ | 238 |
| 56 | H | isoropyl | H | 4-methylphenyl | 243 |
| 57 | H | isopropyl | H | 4-chlorophenyl | 223 |
| 58 | H | isopropyl | H | $n\text{-}C_4H_9$ | 183 |
| 59 | H | isopropyl | H | 2,6-dimethylphenyl | 193–195 |

TABLE 1-continued
Hydroxypyridone-3-carboxamides I
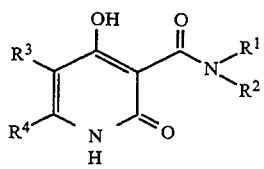
| No. | R¹ | R² | R³ | R⁴ | Melting point [°C.] |
|---|---|---|---|---|---|
| 60 | H | t-butyl | H | 4-CH₃-phenyl | 213–214 |
| 61 | H | t-butyl | H | 4-Cl-phenyl | 226 |
| 62 | H | t-butyl | H | n-C₄H₉ | 209 |
| 63 | H | t-butyl | H | 3-CH₃-phenyl | 178 |
| 64 | H | —CH₂-(3-OCH₃-phenyl) | H | CH₃ | 215 |
| 65 | H | —CH₂-(3,4-diCl-phenyl) | H | CH₃ | 226 |
| 66 | H | —CH₂-(2-CH₃-phenyl) | H | CH₃ | 195 |
| 67 | H | —CH₂-(4-CH₃-phenyl) | H | CH₃ | 233–235 |
| 68 | H | —CH₂-(3-CH₃-phenyl) | H | CH₃ | 178 |
| 69 | —CH₂-(2-F-6-Cl-phenyl) | H | H | CH₃ | 254 |

TABLE 1-continued

Hydroxypyridone-3-carboxamides I

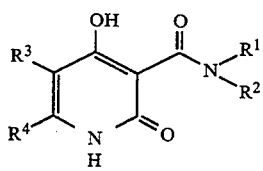

| No. | R¹ | R² | R³ | R⁴ | Melting point [°C.] |
|---|---|---|---|---|---|
| 70 | 2-(4-nitrophenyl)propan-2-yl | H | H | CH₃ | 252 |
| 71 | 3-chlorobenzyl | H | H | CH₃ | 230 |
| 72 | 2-methoxybenzyl | H | H | CH₃ | 210 |
| 73 | H | iso-butyl | H | CH₃ | 170 |
| 74 | H | sec.-butyl | H | CH₃ | 204 |
| 75 | H | 2,6-diethylbenzyl | H | CH₃ | 232–233 |
| 76 | t-butyl | H | H | benzyl | 192 |
| 77 | t-butyl | H | H | 4-methoxyphenyl | 170 |
| 78 | t-butyl | H | H | isopropyl | 218 |
| 79 | cyclopropylmethyl (CH(CH₃)-cyclopropyl) | H | H | 4-isopropylphenyl | 147 |
| 80 | cyclopropylmethyl (CH(CH₃)-cyclopropyl) | H | H | 4-fluorophenyl | 170–173 |
| 81 | cyclopropylmethyl (CH(CH₃)-cyclopropyl) | H | H | benzyl | 122–125 |
| 82 | isopropyl | H | H | 4-isopropylphenyl | 213 |
| 83 | isopropyl | H | H | 4-fluorophenyl | 204–206 |
| 84 | isopropyl | H | H | benzyl | 192 |

TABLE 1-continued

Hydroxypyridone-3-carboxamides I

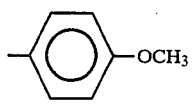

| No. | R¹ | R² | R³ | R⁴ | Melting point [°C.] |
|---|---|---|---|---|---|
| 85 | isopropyl | H | H | 4-methoxyphenyl | 182 |
| 86 | isopropyl | H | H | isopropyl | 165 |
| 87 | isopropyl | H | H | CH₃ | 278 |
| 88 | H | t-butyl | H | CH₃ | 207–210 |
| 89 | H | —CH₂—C₆H₄—C(CH₃)₃ | H | CH₃ | 211 |
| 90 | H | (CH₃)CH—CH₂—C₆H₄—OCH₃ | H | CH₃ | 172 |
| 91 | H | (CH₃)CH-CH₂-CH₂-(3,4-dimethoxyphenyl) | H | CH₃ | 162–166 |
| 92 | H | —C(CH₃)₂—CH₂—C₆H₅ | H | CH₃ | 157–159 |
| 93 | H (on R¹: CH(CH₃)(CH(CH₃)₂)-phenyl) | H | H | CH₃ | 183 |
| 94 | (R¹: C(CH₃)(C₂H₅)-phenyl) | H | H | CH₃ | 148–150 |
| 95 | (R¹: n-butyl-phenyl) | H | H | CH₃ | 198 |
| 96 | (R¹: CH(CH₃)(C₂H₅)-phenyl) | H | H | CH₃ | 167–170 |
| 97 | (R¹: C(CH₃)₃-phenyl) | H | H | CH₃ | 176–177 |

TABLE 1-continued

Hydroxypyridone-3-carboxamides I

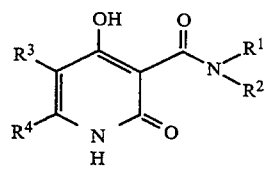

| No. | R¹ | R² | R³ | R⁴ | Melting point [°C.] |
|---|---|---|---|---|---|
| 98 | CH(CH₃)CH₂CH₃-phenyl | H | H | CH₃ | 102–103 |
| 99 | CH₂CH(CH₃)CH₂CH₃-phenyl (iso) | H | H | CH₃ | 118–120 |
| 100 | CH(CH₃)CH₂CH₂-phenyl | H | H | CH₃ | 135–138 |
| 101 | CH₂CH₂CH₂-(4-pyridyl) | H | H | CH₃ | 233–236 |
| 102 | CH₂CH₂CH₂-(2-pyridyl) | H | H | CH₃ | 213 |
| 103 | isobutyl | H | H | CH₃ | 170 |
| 104 | p-chlorobenzyl | H | H | CH₃ | 238 |
| 105 | 2,4-dichlorobenzyl | H | H | CH₃ | 267 |
| 106 | 2-fluorobenzyl | H | H | CH₃ | 182 |
| 107 | 3-fluorobenzyl | H | H | CH₃ | 207–210 |
| 108 | 4-tert-butyl-oxybenzyl | H | H | CH₃ | 175–177 |
| 109 | p-fluorobenzyl | H | H | CH₃ | 232–235 |
| 110 | 2,5-dimethyl-benzyl | H | H | CH₃ | 174 |
| 111 | 2,4-dimethyl-benzyl | H | H | CH₃ | 203 |
| 112 | CH(CH₃)-phenyl (−) form | H | CH₃ | CH₃ | 250 |
| 113 | H | CH(CH₃)-phenyl (−) form | H | CH₃ | 146–148 |
| 114 | H | CH(CH₃)-cyclopropyl | H | CH₃ | 207 |

USE EXAMPLES

The herbicidal action of compounds I according to the invention is demonstrated in greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, plants were used which had been sown in the pots and grown there, or they were grown separately as seedlings and transplanted to the pots a few days before treatment. The plants were grown, depending on growth form, to a height of 3 to 15 cm before being treated with the compounds, suspended or emulsified in water. The application rate for postemergence treatment was 3 kg/ha.

The pots were set up in the greenhouse at temperatures specific to the plant species, viz., from 20° to 35° C., and from 10° to 25° C. The experiments were run for from 2 to 4 weeks. During this period the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments were *Echinochloa crus-galli* and *Centaurea cyanus*.

The compounds of Examples 1, 7, 9, 29 and 31, applied postemergence at a rate of 3 kg/ha, have a very good action on *Echinochloa crus-galli*; compounds 1, 2, 7, 14, 24, 26–28, 34, 35 and 74 are very effective in combating *Centaurea Cyanus*.

We claim:

1. A hydroxypyridonecarboxamide of the formula I,

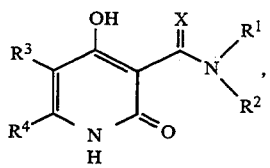

where:

X is oxygen or sulfur;

$R^1$, $R^2$ independently of each other are hydrogen, straight-chain or branched $C_1-C_{25}$-alkyl, $C_3-C_{25}$-alkenyl, $C_3-C_{25}$-alkynyl, $C_3-C_8$-cycloalkyl, $C_3-C_8$-cycloalkyl-$C_1-C_{17}$-alkyl or $C_1-C_{25}$-alkoxy, the organic radicals being optionally substituted by halogen, cyano, $C_1-C_5$-alkylcarbonyl, $C_1-C_5$-alkoxycarbonyl, $C_1-C_6$-alkoxy, $C_1-C_6$-haloalkoxy, $C_1-C_6$-alkylthio, or $C_1-C_6$-haloalkylthio;

$R^3$ is hydrogen, $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, halogen or nitro;

$R^4$ is $C_1-C_{10}$-alkyl, $C_2-C_{10}$-alkenyl, $C_2-C_{10}$-alkynyl, $C_3-C_{10}$-cycloalkyl, $C_1-C_{10}$-alkoxy, $C_1-C_{10}$-alkylthio, phenyl, the said radicals being optionally substituted by halogen, $C_1-C_3$-alkyl, $C_1-C_3$-haloalkyl, $C_1-C_3$-alkoxy, $C_1-C_3$-haloalkoxy, $C_1-C_3$-haloalkylthio or phenyl optionally substituted by a member selected from the group consisting of halogen, $C_1-C_3$-alkyl, $C_1-C_3$-haloalkyl, $C_1-C_3$-haloalkoxy and $C_1-C_3$-alkoxyl;

and environmentally acceptable salts thereof, with the exception of 6-methyl-4-hydroxypyrid-2-one-3-carboxamide and 6-methyl-4-hydroxypyrid-2-one-3-carboxylic acid-tert-butylamide.

2. A hydroxypyridonecarboxamide of the formula I as set forth in claim 1, where X and the radicals $R^1$ to $R^4$ have the following meanings:

X is oxygen or sulfur;

$R^1$ is hydrogen;

$R^2$ is branched or straight-chain $C_1-C_{15}$-alkyl, $C_3-C_{15}$-alkenyl, $C_3-C_{15}$-alkynyl, $C_1-C_{15}$-alkoxy or $C_3-C_6$-cycloalkyl, and these radicals are optionally substituted by halogen, $C_1-C_3$-alkoxy, $C_1-C_3$-haloalkoxy or phenyl which is optionally substituted by from one to five halogen atoms and/or from one to three members selected from the group consisting of cyano, nitro, $C_1-C_4$-alkyl, $C_1-C_4$-alkoxy, $C_1-C_4$-haloalkyl or $C_1-C_4$-haloalkoxy;

$R^3$ is hydrogen, $C_1-C_3$-alkyl, $C_1-C_3$-haloalkyl, $C_1-C_3$-alkoxy, $C_1-C_3$-haloalkoxy, $C_1-C_3$-alkylthio, $C_1-C_3$-haloalkylthio, halogen or nitro;

$R^4$ is $C_1-C_6$-alkyl, $C_2-C_6$-alkenyl, $C_2-C_6$-alkynyl, $C_3-C_6$-cycloalkyl, $C_1-C_6$-alkoxy, $C_1-C_6$-alkylthio or phenyl and the said radicals substituted by halogen, $C_1-C_3$-alkyl, $C_1-C_3$-haloalkyl, $C_1-C_3$-alkoxy, $C_1-C_3$-haloalkoxy, $C_1-C_3$-haloalkylthio, or phenyl optionally substituted by a member selected from the group consisting of halogen, $C_1-C_3$-alkyl, $C_1-C_3$-alkoxy, $C_1-C_3$-haloalkyl or $C_1-C_3$-haloalkoxy.

3. A hydroxypyridonecarboxamide of the formula I as set forth in claim 1, where X and the radicals $R^1$ to $R^4$ have the following meanings:

X is oxygen or sulfur;

$R^1$ is hydrogen;

$R^2$ is branched or straight-chain $C_1-C_6$-alkyl, $C_3-C_6$-alkenyl, $C_3-C_6$-alkynyl or $C_1-C_4$-alkoxy;

$R^3$ is hydrogen, $C_1-C_3$-alkyl, $C_1-C_3$-haloalkyl, $C_1-C_3$-alkoxy, halogen or nitro;

$R^4$ is $C_1-C_6$-alkyl or phenyl, each of which is optionally substituted by from one to three radicals selected from the group consisting of halogen, $C_1-C_3$-alkoxy, $C_1-C_3$-haloalkoxy, $C_1-C_3$-alkylthio, $C_1-C_3$-haloalkylthio or substituted or unsubstituted phenyl optionally substituted by a member selected from the group consisting of halogen, $C_1-C_3$-alkyl, $C_1-C_3$-alkoxy, $C_1-C_3$-haloalkyl or $C_1-C_3$-haloalkoxy.

4. A herbicidal composition comprising an effective amount of a hydroxypyridonecarboxamide of the formula I as set forth in claim 1 and conventional inert additives.

5. A method of combating the growth of unwanted plants, wherein the unwanted plants and/or their habitat are treated with a herbicidally effective amount of a hydroxypyridonecarboxamide of the formula I

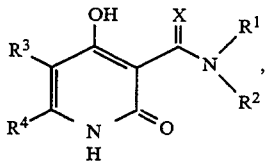

where:

X is oxygen or sulfur;

$R^1$, $R^2$ independently of each other are hydrogen, straight-chain or branched $C_1$–$C_{25}$-alkyl, $C_3$–$C_{25}$-alkenyl, $C_3$–$C_{25}$-alkynyl, $C_3$–$C_8$-cycloalkyl, $C_3$–$C_8$-cycloalkyl-$C_1$–$C_{17}$-alkyl or $C_1$–$C_{25}$-alkoxy, the organic radicals being optionally substituted by halogen, cyano, $C_1$–$C_5$-alkylcarbonyl, $C_1$–$C_5$-alkoxycarbonyl, $C_1$–$C_6$-alkoxy, $C_1$–$C_6$-haloalkoxy, $C_1$–$C_6$-alkylthio, $C_1$–$C_6$-haloalkylthio, or phenyl which in turn is optionally substituted by from one to five halogen atoms and/or from one to three members selected from the group consisting of cyano, nitro, $C_1$–$C_4$-alkyl, $C_1$–$C_4$-alkoxy, $C_1$–$C_4$-haloalkyl or $C_1$–$C_4$-haloalkoxy;

$R^3$ is hydrogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen or nitro; $R^4$ is $C_1$–$C_{10}$-alkyl, $C_2$–$C_{10}$-alkenyl, $C_2$–$C_{10}$-alkynyl, $C_3$–$C_{10}$-cycloalkyl, $C_1$–$C_{10}$-alkoxy, $C_1$–$C_{10}$-alkylthio, phenyl, the said radicals being optionally substituted by halogen, $C_1$–$C_3$-alkyl, $C_1$–$C_3$-haloalkyl, $C_1$–$C_3$-alkoxy, $C_1$–$C_3$-haloalkoxy, $C_1$–$C_3$-haloalkylthio, or phenyl optionally substituted by a member selected from the group consisting of halogen, $C_1$–$C_3$-alkyl, $C_1$–$C_3$-alkoxy, $C_1$–$C_3$-haloalkyl and $C_1$–$C_3$-haloalkoxy.

6. A hydroxypyridonecarboxamide of the formula I as set forth in claim 1, wherein X is oxygen, $R^1$ is hydrogen, $R^2$ is isopropyl, $R^3$ is hydrogen, and $R^4$ is methyl.

7. A method of combating the growth of unwanted plants, wherein the unwanted plants and/or their habitat are treated with a herbicidally effective amount of a hydroxypyridonecarboxamide of the formula I as defined in claim 2.

8. A method of combating the growth of unwanted plants, wherein the unwanted plants and/or their habitat are treated with a herbicidally effective amount of a hydroxypyridonecarboxamide of the formula I as defined in claim 3.

* * * * *